United States Patent [19]

Kurz et al.

[11] 4,058,373
[45] Nov. 15, 1977

[54] COMBUSTIBLE GAS-IN-OIL DETECTOR

[75] Inventors: Robert A. Kurz, West Middlesex; Donald K. Whirlow, Murrysville, both of Pa.

[73] Assignee: Electric Power Research Institute, Palo Alto, Calif.

[21] Appl. No.: 770,196

[22] Filed: Feb. 18, 1977

[51] Int. Cl.² ............................................. B01D 59/10
[52] U.S. Cl. .......................................... 55/16; 55/158
[58] Field of Search ...................... 55/16, 158, 40, 208; 73/1 G, 23, 23.1

[56] References Cited

U.S. PATENT DOCUMENTS

| 3,651,616 | 3/1972 | Blanchard | 55/16 |
| 3,785,121 | 1/1974 | Phelph | 55/53 |
| 3,926,561 | 12/1975 | Lucero | 55/16 |

Primary Examiner—John Adee
Assistant Examiner—E. Rollins Cross
Attorney, Agent, or Firm—Flehr, Hohbach, Test, Albritton & Herbert

[57] ABSTRACT

Method and apparatus is disclosed for extracting and analyzing gas from a body of liquid such as oil in an electrical transformer. The oil is continuously moved by thermosiphonic action through a conduit in which a gas permeation cell is mounted. Oil within the conduit is air cooled to create a temperature gradient relative to the body of liquid for establishing the thermosiphonic movement. The permeation cell comprises a semipermeable membrane supported about an elongate porous tube mounted concentric within the conduit so that gas contained within the liquid permeates through the membrane and into a chamber within the cell. An inert carrier gas is injected into and out of the chamber for carrying the permeating gas to a gas detector-analyzer unit.

15 Claims, 4 Drawing Figures

COMBUSTIBLE GAS-IN-OIL DETECTOR

BACKGROUND OF THE INVENTION

This invention relates in general to gas detection methods and equipment, and in particular relates to the detection of gas absorbed in a body liquid, such as gases which are formed in oil-filled electrical apparatus.

Oil filled electrical apparatus such as electrical transformers in many instances generate gases from faults or failures in the apparatus. For example, electrical arcing and discharge, overheating, breakdown of cellulosic paper or heating of copper bus bars within oil will produce gases such as hydrogen, carbon monoxide and carbon dioxide.

It has heretofore been known to analyze the gases in oil-filled electrical apparatus to indicate the presence and nature of incipient faults of the foregoing character. One method which has been employed for this purpose is to periodically drain an oil sample from the transformer or other apparatus into containers, with the gases then being extracted from the sample by vacuum. The extracted gases are then passed through a chromatograph for analysis. Another recipient fault detection system includes equipment which automatically and periodically drains oil from a transformer into a chamber from which gas is extracted and analyzed in a chromatograph, but such equipment is complicated in design and construction and is relatively expensive. Mechanical apparatus has also been employed to pump oil from a transformer through a gas permeation cell. However, the moving parts required in apparatus of this character introduce wear and maintenance problems and are a source of malfunction. It would be desirable to provide a system which will extract gas from a body of liquid continuously without the requirement for moving parts, and without the need for a separate power source.

OBJECTS AND SUMMARY OF THE INVENTION

It is a general object of the invention to provide new and improved method and apparatus for extracting and analyzing gas from a body of liquid, such as oil-filled electrical apparatus.

Another object is to provide method and apparatus of the character described which is highly simplified and inexpensive in design and construction and which employs no moving parts or separate power source for extracting gas from the liquid.

Another object is to provide method and apparatus of the character described which moves a sample of liquid by thermosiphonic action about a permeation cell through which gas in the liquid permeates into a chamber, and in which the gas is moved from the chamber for subsequent analysis.

Another object is to provide method and apparatus of the character described in which the permeation cell is configured to provide a semi-permeable surface area which is large in relation to the overall size of the cell.

The invention in summary includes method and apparatus in which liquid is moved by thermosiphonic action through a conduit about a gas permeation cell. A portion of the conduit is cooled for creating a temperature gradient which creates the thermosiphonic action. The gas permeation cell has a semi-permeable membrane which encloses a hollow chamber. Gas absorbed in the liquid permeates through the membrane into the chamber. Means is provided for moving gas from the chamber for subsequent analysis.

The foregoing and additional objects and features of the invention will become apparent from the following description in which the several embodiments have been set forth in detail in conjunction with the accompanying drawings.

DESCRIPTION OF THE PREFERRED EMBODIMENTS

Figure 1:
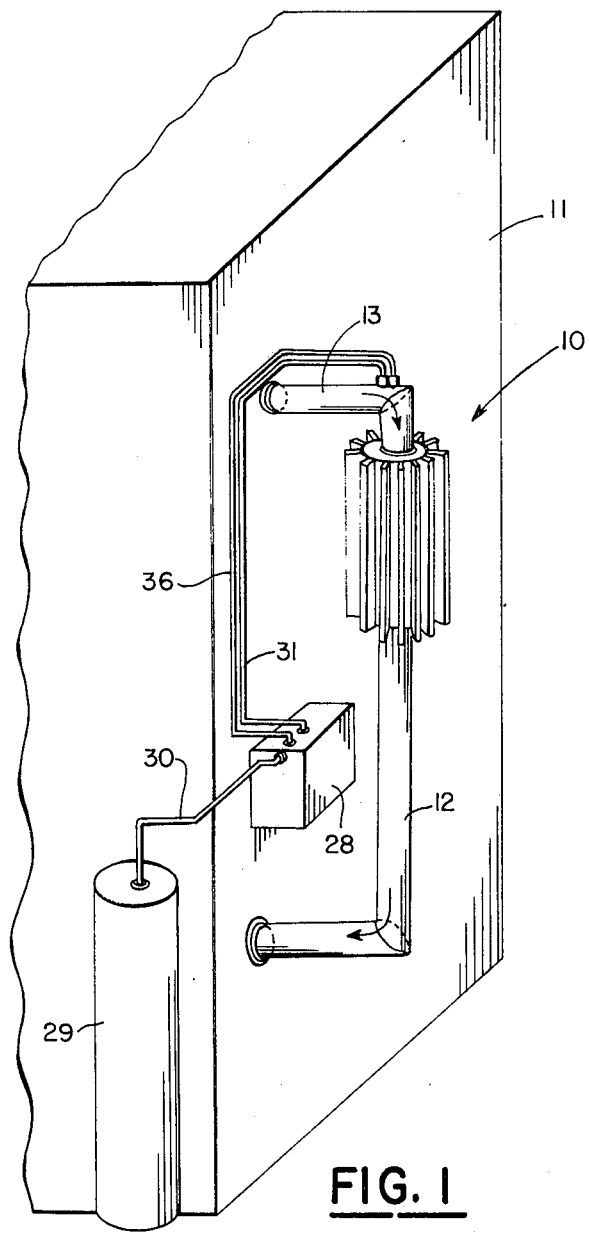
FIG. 1 is a perspective view of apparatus of the invention shown in use with an electrical transformer.
Figure 2:
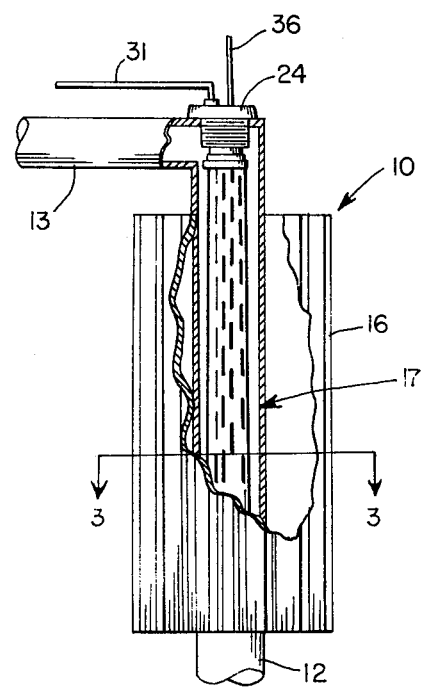
FIG. 2 is an elevational view to an enlarged scale, partially broken away, of the apparatus of FIG. 1.
Figure 3:
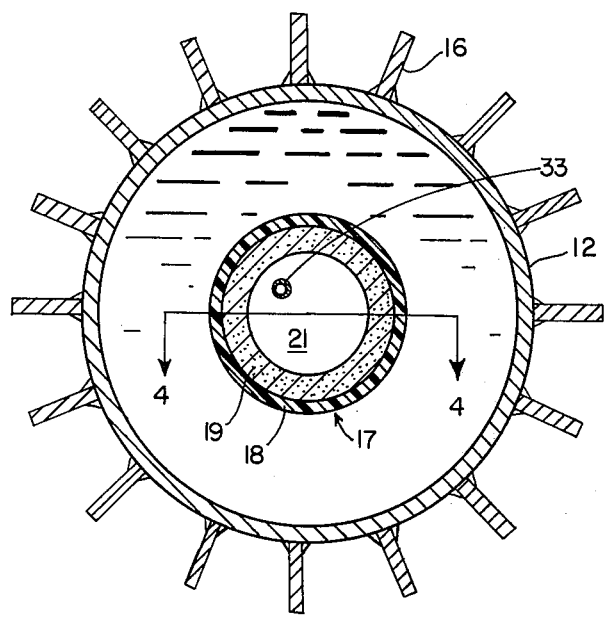
FIG. 3 is a cross section view taken along the line 3—3 of FIG. 2.
Figure 4:
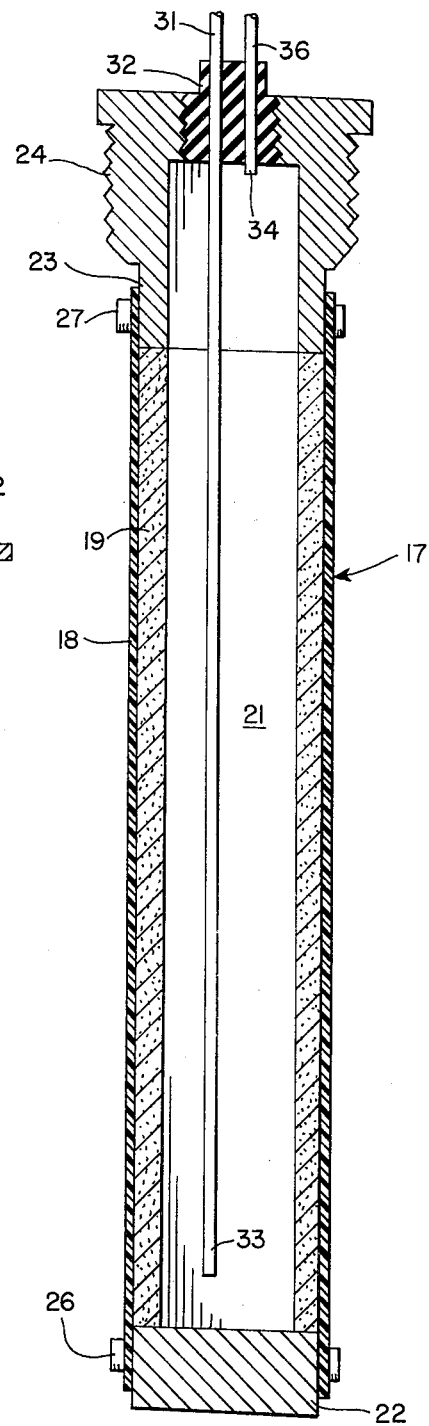
FIG. 4 is an axial section view to an enlarged scale taken along the line 4—4 of FIG. 3.

In the drawing FIG. 1 illustrates generally at 10 apparatus for extracting and analyzing gas which is absorbed within oil contained within an electrical transformer 11. While the invention will be described in relation to an oil-filled electrical transformer it is understood that the invention will also have application for extracting gas from other oil or liquid-filled apparatus. In the illustrated embodiment, apparatus 10 is specifically employed for the detection of incipient faults in the transformer.

Apparatus 10 includes an upstanding pipe or conduit 12 connected at its upper and lower ends through branch conduits 13, 14 with the transformer shell for communication with oil contained therein. The three conduits direct the oil contained therein along a path leading in a loop externally from and returning to the transformer.

Means is provided for cooling oil within a portion of the upstanding conduit to a temperature below that of the oil within the transformer. The cooling means includes a plurality of radially extending vertical metal fins 16 mounted about a section of the conduit. Heat is transferred from the oil through the conduit and fins to ambient air so as to create a temperature gradient along the path of the oil. The differential in oil density created by this temperature gradient causes the oil to continuously move by thermosiphonic action from the upper level of the transformer down through conduit 12 for return into the lower level. Oil movement is thereby achieved without a pump or other moving parts and without any separate power source.

An elongate tubular gas permeation call 17 is mounted concentrically within the upper end of conduit 12. The cell is radially spaced from the conduit so that the cell is enclosed by and in contact with the oil. Permeation cell 17 includes a semi-permeable membrane 18 mounted about a tubular porous support 19. Preferably membrane 18 comprises a thin polymeric material which will pass lower molecular weight gases such as hydrogen, carbon monoxide and carbon dioxide. A membrane comprised of silicone rubber having a thickness on the order of 18 mils is suitable for this purpose. Tubular support 19 serves to provide mechanical support for the membrane while passing the permeating gas into a cylindrical chamber 21 within the cell. The support 19 is formed of a suitable material such as porous metal, and is mounted between a pair of metal rings 22, 23. The ring 23 is affixed to an adapter fitting 24 which is threaded into an opening formed at the juncture between conduits 12 and 13. A pair of retaining rings 26, 27 are secured about opposite ends of the membrane for clamping the membrane between the metal rings.

Gas which permeates through the cell into chamber 21 is extracted and moved to a suitable gas detector-analyzer unit 28, which preferable comprises a gas chromatograph. The permeating gas is extracted from the chamber by means of a carrier gas, a supply of which is contained with a gas tank 29 coupled with unit 28 through conduit 30. The carrier gas is an inert gas of known composition, such as nitrogen or argon. Analyzer unit 28 pumps the carrier gas through an inlet tube 31 leading into permeation cell 17 and through a resilient gas-tight plug 32 which is threaded into adapter 24. The inlet tube extends through the chamber with its open end 33 disposed at the lower end of the cell. Carrier gas which is injected into the cell moves upwardly and carries the permeating gas out through the open end 34 of an exit tube 36 which leads through plug 32. The exit tube directs the gases back to the analyzer unit which operates in a conventional manner to detect the presence and nature of the permeating gas.

The use and method of operation of the invention is as follows. Assuming that the oil within transformer 11 is at a temperature of 80°-85° C, ambient air surrounding cooling fins 16 cools the oil within upright conduit 12 sufficient to create a temperature differential on the order of 10°-20° C. The greater density of the cooler oil in the conduit creates a thermosiphonic action which causes the oil to move from the transformer down through conduit 12 for return in a continuous steady-state flow. Gas absorbed within the oil, such as gas formed from incipient faults, is moved about and in contact with membrane 18 of the permeation cell. The gas permeates through the membrane and through porous support 19 into chamber 21. Detector-analyzer unit 28 is operated to continuously pump a nitrogen carrier gas through inlet tube 31 so as to scavenge the permeating gas from the chamber and carry it back to analyzer unit 28 through exit tube 36. The analyzer unit is operated to continuously monitor and detect the character of the sampled gases and to provide an indication when a particular gas, e.g., hydrogen, carbon monoxide and/or carbon dioxide, is present in the sample so that an incipient transformer fault can be diagnosed.

From the foregoing it will be seen that there has been provided new and improved method and apparatus for extracting and analyzing gas from a body of liquid. The liquid is moved along a gas permeation cell continuously and without the requirement for moving parts or a separate power source so that the system cost is minimal and problems of wear, maintenance and mechanical malfunction are obviated. The gas permeation cell is in a configuration which provides a relatively large permeation area relative to its overall dimensions. The system therefore is relatively simple and inexpensive in design and construction while providing for continuous and highly reliable gas detection.

While the foregoing embodiments are presently considered to be preferred it is understood that numerous variations and modifications may be made therein by those skilled in the art and it is intended to cover in the appendant claims all such variations and modifications as fall within the true spirit and scope of the invention.

What is claimed is:

1. In a system for extracting and analyzing gas carried in a body of liquid, the combination of conduit means for directing a portion of the liquid in a path leading externally from the body and returning thereto, means for cooling the liquid in a portion of the conduit means which is external of the body for creating a temperature gradient along said path for causing the liquid to move through the conduit means by thermosiphonic action, means forming a hollow chamber within a portion of the conduit means with the chamber having semi-permeable outer wall means for passing gas from the liquid into the chamber, and means for moving gas from the chamber for subsequent analysis.

2. A system as in claim 1 in which the outer wall means of the chamber includes an elongate cylindrical shell mounted in radially spaced-apart relationship within the conduit means with liquid contained therein surrounding the cylindrical shell.

3. A system as in claim 2 in which the cylindrical shell includes a support tube of a porous material together with a membrane of semi-permerable material mounted about the support tube.

4. A system as in claim 1 in which the conduit means includes an upright section and means forming a heat exchange surface on the upright section for transferring heat to air surrounding the heat exchange surface for cooling fluid within the upright section.

5. A system as in claim 4 in which the means forming a heat exchange surface includes a plurality of radially extending fins mounted about the upright section.

6. A system as in claim 1 in which the means for moving the gas from the chamber includes an inlet tube having an open end extending into the chamber together with an outlet tube having an open end extending into the chamber, and means for moving a carrier gas through the inlet tube, into the chamber and through the outlet tube whereby gas which permeates into the chamber from the fluid is moved along with the carrier gas through the outlet tube.

7. A system as in claim 6 which includes means connected with the outlet tube for analyzing and determining the character of the gas being carried by the carrier gas.

8. Apparatus for detecting gas within an oil-filled structure, including an upright conduit having its upper and lower ends connected in fluid communication with the oil in the structure, means for cooling at least a portion of the upright conduit and thereby cooling oil contained therein to a temperature lower than the temperature of oil within the structure for causing thermosiphonic movement of oil from the structure through the upper end of the conduit and back to the structure through the lower end, an elongate cell wall enclosing an inner chamber with the outer wall being formed at least in part of a semi-permeable material for permeating gas into the chamber from oil surrounding the cell, and means for extracting said gas from the cell.

9. Apparatus as in claim 8 in which the cooling means includes a plurality of vertically elongate, radially extending fins mounted about a portion of the upright conduit.

10. Apparatus as in claim 8 in which the outer wall of the cell includes a support wall formed of a porous metal together with a semi-permeable polymeric membrane carried about the support wall.

11. Apparatus as in claim 10 in which said membrane is formed of a silicone rubber.

12. Apparatus as in claim 8 in which said extraction means includes means coupled with the cell for injecting a carrier gas into the chamber and for carrying said permeating gas out of the chamber.

13. In a method for analyzing gas in a body of liquid, the steps of directing liquid from the body along a path externally thereof, creating a temperature differential between liquid in the path relative to liquid in the body whereby the liquid moves from the body through the path by thermosiphonic action, directing the liquid moving in the path into contact with one side of a semi-permeable membrane, causing gas in the liquid to permeate through the membrane, and collecting gas which permeates through the membrane for subsequent analysis.

14. A method as in claim 13 in which the liquid is directed from the body along an upstanding path, and the temperature differential is created by cooling liquid in a portion of the upstanding path to a temperature below the temperature of the liquid in the body to establish liquid movement by thermosiphonic action.

15. A method as in claim 13 in which the semi-permeable membrane encloses a chamber with the membrane being surrounded by liquid in the path whereby gas permeates through the membrane into the chamber, and the gas is collected by directing a carrier gas into and out of the chamber for carrying said permeating gas therewith.

* * * * *